United States Patent [19]

Schwentker

[11] 4,454,870

[45] Jun. 19, 1984

[54] HALO JIG

[75] Inventor: Edwards P. Schwentker, Hershey, Pa.

[73] Assignee: Ace Medical Company, Los Angeles, Calif.

[21] Appl. No.: 408,733

[22] Filed: Aug. 17, 1982

[51] Int. Cl.³ .......................... A61F 5/04; A61H 1/02
[52] U.S. Cl. ...................................... 128/75; 128/82; 128/133
[58] Field of Search .............. 128/75, 69, 84 R, 84 C, 128/87 R, 87 B, 133, 134, 68, 82, 83

[56] References Cited

U.S. PATENT DOCUMENTS

| | | | |
|---|---|---|---|
| 3,897,777 | 8/1975 | Morrison | 128/133 |
| 4,034,748 | 7/1977 | Winner | 128/134 X |
| 4,141,368 | 2/1979 | Meyer | 128/134 X |
| 4,161,946 | 7/1979 | Zuesse | 128/75 |
| 4,194,501 | 3/1980 | Watt | 128/75 |
| 4,220,147 | 9/1980 | Allen | 128/75 |

OTHER PUBLICATIONS

"Total Cervical Spine Fusion for Neck Paralysis" by J. Perry et al., The Journal of Bone & Joint Surgery, vol. 41-A, No. 1, Jan. 1959, pp. 37-60.

"Cervical Orthoses" by Rollin M. Johnson et al., The Journal of Bone & Joint Surgery, vol. 59-A, No. 3, Apr. 1977, pp. 332-339.

Primary Examiner—Ronald L. Frinks
Attorney, Agent, or Firm—Hubbard & Stetina

[57] ABSTRACT

A jig for fitting a halo to a patient with a cervical injury, which supports the patient's head during the fitting, and leaves the surgeon's hands free for manipulation and stabilization, is disclosed.

3 Claims, 11 Drawing Figures

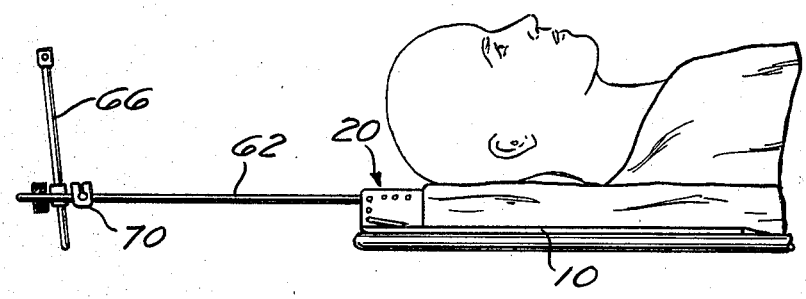
Fig. 4
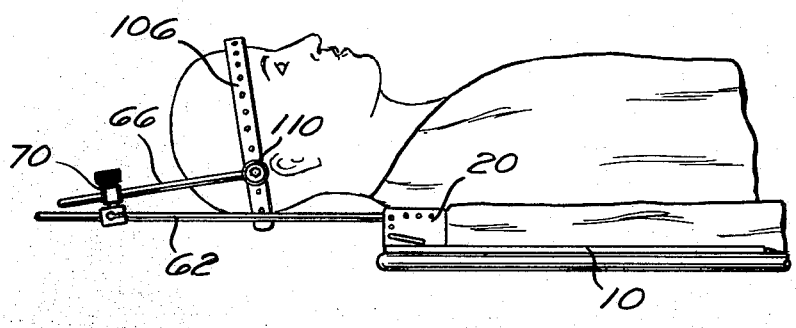
Fig. 5
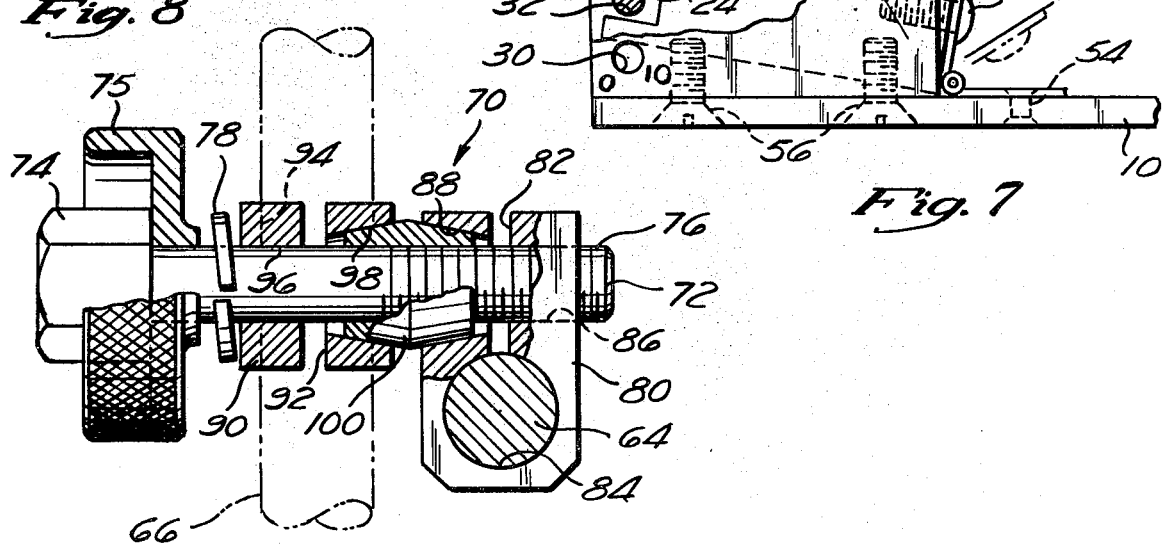
Fig. 7
Fig. 8

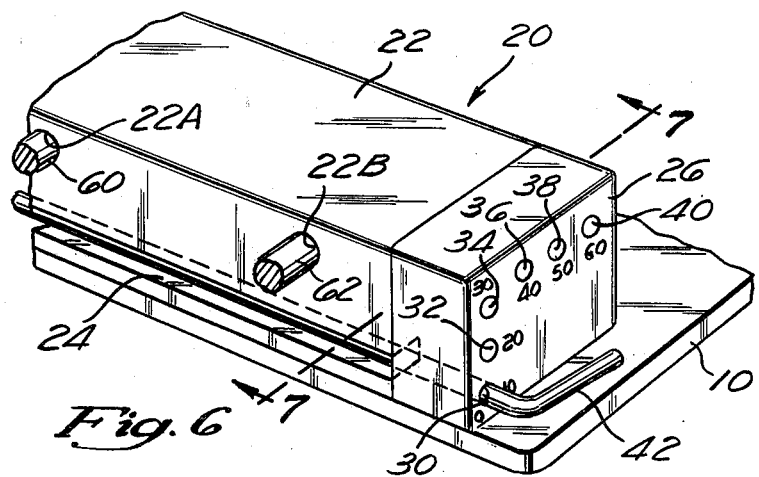

HALO JIG

TECHNICAL GROUND

This invention relates to orthopedic appliances generally, and more specifically, to orthopedic appliances for use by surgeons to fit a halo ring to a patient having a cervical defect or injury, and still more specifically to a jig for fitting the halo ring on such patient while supporting the patient's head and leaving the surgeon free to manipulate the device and the patient's head.

BACKGROUND ART

The cranial halo was first reported by Perry and Nickel in 1959. (Perry J., Nickel V. L., Total Cervical Spine Fusion for Neck Paralysis, J. Bone Joint Surg. 1959; 41A:37.) Since then, it has become widely accepted for a secured fixation and versatility. The halo may be utilized to provide skeletal traction for the entire spine, and combined with a cast or a vest it provides the best available external control of cervical spine instability. Control adjustments may be made for traction, angulation, rotation, and translation. Once locked into position, the halo vest or halo cast will prevent over 95% of the cervical spine motion in all planes; a degree of rigidity far superior to that provided by conventional orthoses. (Johnson, R. M., Hart, D. L., Simmons, E. F., Armsby, G. R., Southwick, W. O., Cervical Orthoses, J. Bone Joint Surg. 1977; 59A:322.)

Unfortunately, the significant advantages of this halo have been partially offset by the difficulties in its application. Initially published methods for applying the halo (Nickel, D. L., Perry, J., Garrett, A., Application of the Halo, Orthat. Prosthet. 1960; pp. 31-35, and Young, R., Thomassen, E. H., Step By Step Procedure for Applying the Halo Ring, Orthop. Rev., 1974; 3(6):62-64) have been cumbersome and time-consuming in practice. By these methods, the patient's head is either hand-held or precariously supported on a narrow board, and the halo ring is supported by yet another pair of hands and a set of positioning pins and plates. The lack of rigidity makes exact positioning of the ring difficult to obtain. Recently, a report by Weiss and Wilmot describes a device which supports the head during halo application, but their device does not support the halo ring and can only be used with a patient on a Stryker frame. (Weiss, M. S., Wilmot, C. B., Head Positioning Device for Applying Halo Traction, Arch. Phys. Med. Rehabil., 1981; 62:89.) The present invention, known as the Hershey Halo Jig (Trade mark), was developed to increase the speed, accuracy, and safety of the halo application. This device has been used successfully on an experimental basis at the Milton S. Hershey Medical Center since the first prototype was developed in March 1979. Over this period of time, a number of variations have been made based upon experimental usage and experience. The present invention constitutes the final design, as presently contemplated, of this improved halo jig.

Statement of the Invention

The present invention consists of a rectangular block which is securely attached to a flat plate. This plate, sometimes referred to as a tongue, is about 24 inches in length, typically, and is designed to slip under the mattress of a standard hospital litter or operating room table. Once placed, the jig is stabilized by the patient's body weight. Two steel rods, typically about ⅜ inch diameter, slide into parallel holes in the block. The rods are, in the exemplary embodiment, about 2 and ⅛ inch apart, and the rods, together, serve as a support for the patient's head during installation of the halo.

The rod-holding center portion of the block is hinged to permit adjustment of the inclination of the head support rods just referred to. Inclination adjustment allows compensation for varying thickness of mattress, and permits the patient's neck to be placed in the most stable position of the flexion-extension range in cases where there is vertebral column instability.

After the jig has been appropriately adjusted, the patient is carefully lifted and moved cephalad until the patient's head is resting on the head supporting rods and the block is just beneath the base of the neck. If there is spinal instability, the transfer is made with the surgeon at the patient's head applying traction and maintaining spinal alignment.

A cross bar connects the two head support rods, and from this extends a halo support rod which supports the halo ring during installation. The halo support rod is freely adjustable in three planes. An appropriate size halo ring is selected and threaded over the rods and around the patient's head. The surgeon holds the ring in position while the assistant attaches it to the halo support rod and locks the halo support rigidly into place.

Both the patient's head and the halo ring are now securely supported, the surgeon's and the assistant's hands are free and the entire circumference of the halo ring is completely accessible with the single exception of the point of attachment of the halo support rod. Skull pin insertion can now be quickly accomplished by the standard technique, which is well-known in the orthopedic profession.

After the skull pins have been placed and torqued, the halo support rod is detached from the halo. The surgeon holds the patient's head by the halo ring and maintains spinal alignment while the assistant withdraws the head support rods from the block and out from between the patient's head and ring. The patient may then be backed onto the litter or table or transferred to a Stryker frame or standard bed. The procedure is then complete.

Application of the halo vest assembly is greatly simplified by use of the jig. The vest and connecting hardware applied before placing the patient on the jig. Following halo application by the technique described, the ring may be simply attached to the vest prior to withdrawal of the head support rods. Proper spinal alignment is thus automatically obtained.

A major concern in developing the halo jig was the safety of the halo application, particularly in cases of spinal instability. The halo jig of this invention answers this concern, for it is self-stabilized by the patient's body weight. The patient, the jig and the table or litter upon which the patient rests becomes one integral unit during the installation of the halo ring. The risk of sudden catastrophic movement of the cervical spine is, thus, virtually eliminated. In experimental use at the Milton S. Hershey Medical Center of the Pennsylvania State University, the jig has proven its safety and it has, in addition, substantially improve the speed and accuracy of the application procedure. The end result has been an increase in the usefulness of the cranial halo ring.

BRIEF DISCUSSION OF THE DRAWINGS

FIG. 4 shows the apparatus of this invention in position for use upon a patient, the patient being shown placed upon a litter or operating table.

FIG. 5 shows the patient in position following application of the halo ring according to this invention.

FIG. 6 is a detailed view of the attachment block and a means for adjusting the angle of the head support rods, in perspective view from the distal side, as opposed to the proximal view of the same block in FIG. 3.

FIG. 7 is a cross-sectional view of the block attached to the plate or tongue taken substantially along lines 7—7 of FIG. 6, showing the angular adjustment of the head support rods and showing, in phantom line, a second angular adjustment thereof.

FIG. 8 is an enlarged detailed view, in partial cross-section, of the clamp which attaches the cross bar to the halo support rod, showing the internal structure in detail.

FIG. 9 is an enlarged view, in partial cross-section, showing the internal structure of the clamp for attaching the halo ring to the halo support rod.

FIG. 10 is a top view of the apparatus of this invention showing the halo ring, in phantom line, attached thereto.

FIG. 11 is a side view, as taken with respect to FIG. 10, of the apparatus of this invention, showing, in phantom line, the head support rods in a raised angular position.

DESCRIPTION OF THE BEST MODE

Figure 1:
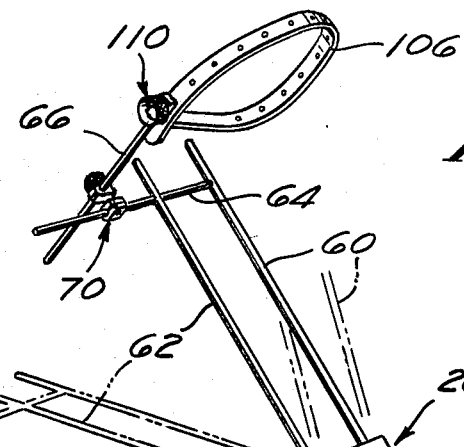
FIG. 1 is a perspective view of a halo jig of this invention showing the major components thereof.

Referring first to FIG. 1, the overall construction of the apparatus of this invention is most easily understood. In its major components, the invention comprises a plate or tongue 10 which, as previously described, is adapted to be slid under the mattress of a litter or operating table. Block 20, which will be described in detail hereinafter, is securely attached to the distal end of the tongue or plate 10. The block assembly 20 receives a pair of head support rods 60 and 62 which, in turn, supports a cross bar 64 and, by means of clamp 70, a halo support rod 66 which, in turn, by means of clamp 110, supports a halo ring 106. The head support rod assembly is shown, in phantom line, in a substantially horizontal position, with respect to the plate, in solid line in a raised angular position, and in partial phantom line, in an even greater angular position.

Figure 2:
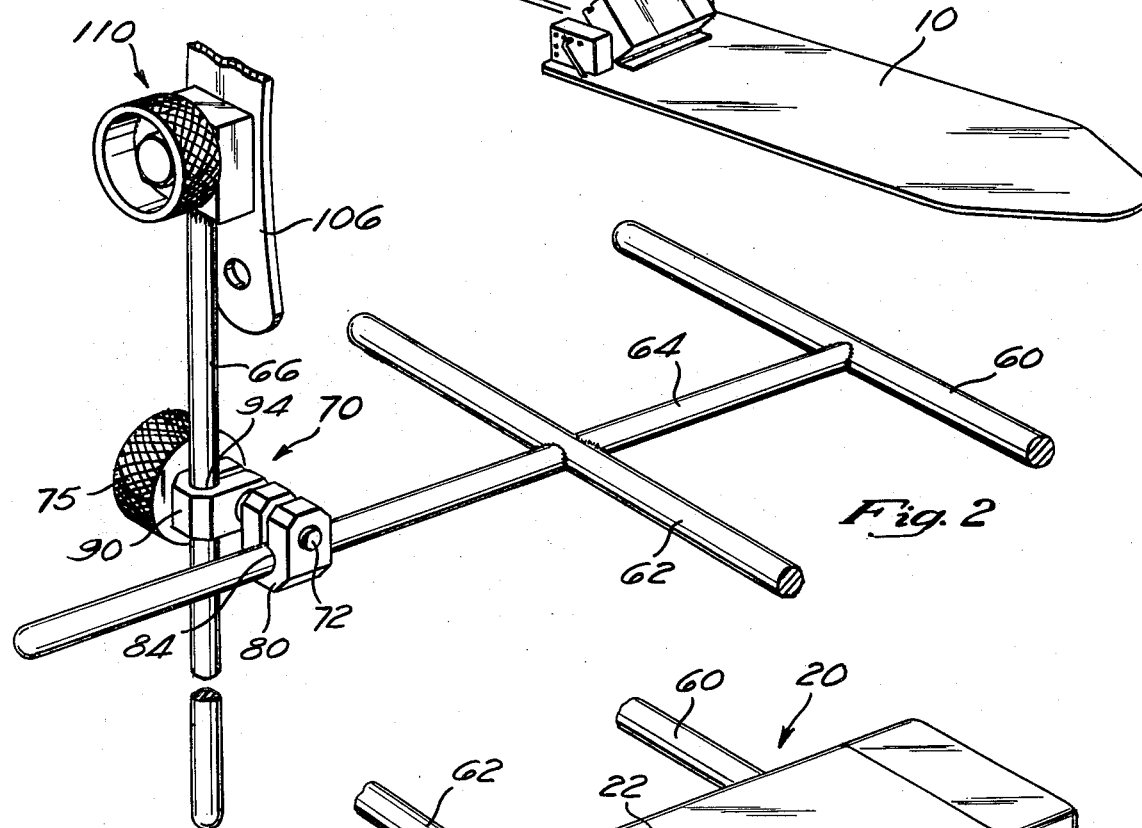
FIG. 2 is a perspective view of the head support rods, the cross bar, and a halo support rod, showing the typical attachment of the halo ring.

The details of the head support rod, cross bar and halo support rod assembly and the related clamps is shown in greater detail in FIG. 2. It will be seen that the head support rods 60 and 62 extend generally parallel one to another and the cross bar 64 extends between the head support rods and out to one side thereof. Cross bar may, of course, extend on both sides but usually there is no advantage in doing so. It is immaterial whether the cross bar 64 extends to one side or to the other. A clamp 70, which will be described in detail, holds a halo support rod 66 in a rigid position. By loosening the clamp 70, however, the halo support rod 66 may be adjusted at any angle in two planes. A halo ring 106 is shown attached by means of clamp 110 to the end of the halo support rod 66. By loosening the clamp 110, the halo support ring may be adjusted to any angle in a single plane with respect to the halo support rod 66. Thus, by means of clamps 70 and 110, and their inter-relationship with the cross bar 64 and the halo support rod 66, the halo ring may be supported at any angle in three planes.

Figure 3:
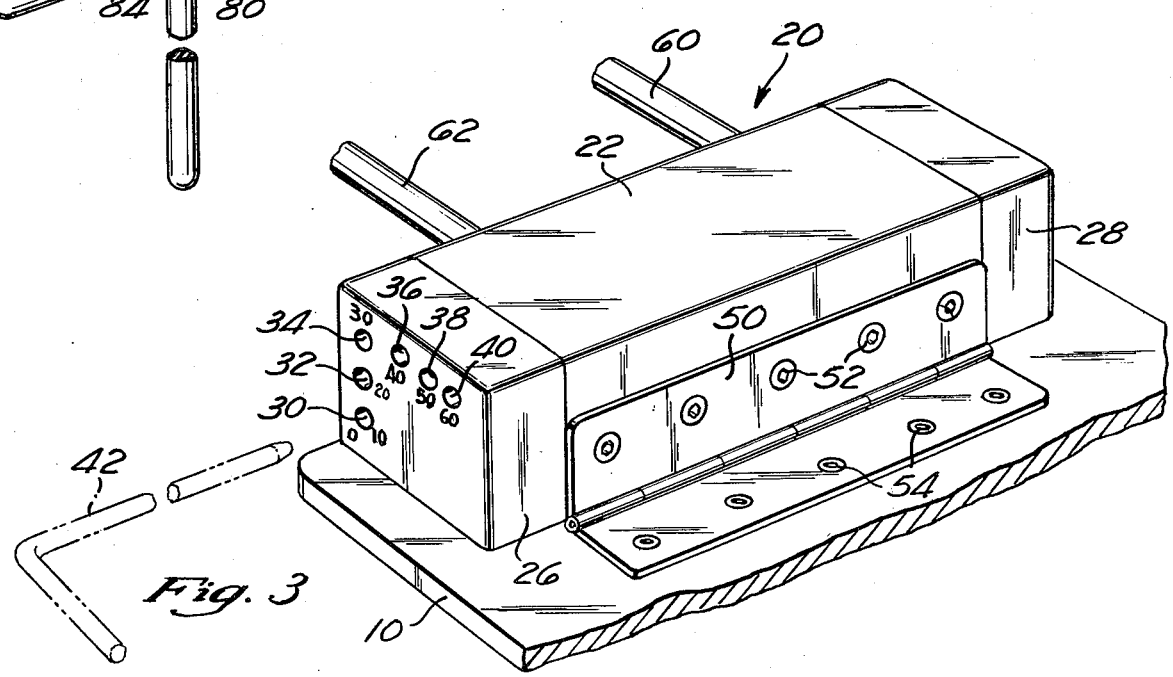
FIG. 3 shows another fragment of the apparatus of this invention, showing in detail the pivotal block, its hinging attachment to the plate or tongue, and the means for adjusting the angle of the head support rods.

FIG. 3 is a perspective view which most easily depicts the structure of the block 20 which comprises, as major components, a pivotal block portion 22, with recesses 22A and 22B to receive the ends of the head support rods 60 and 62, and a block or passageway 24 to permit angular adjustment as will be described. The block assembly also includes in block 26 and another in block 28 which cooperate with a pin as will be described to permit adjustment of the angle of the support rods with respect to the tongue or plate 10.

Angular adjustment is provided by apertures 30, 32, 34, 36, 38 and 40, in the block 26 and, preferably, corresponding apertures in the block 28 through which a pin 42 extends. As best shown in FIGS. 6 and 7, the pin 42 also extends through the slot or passageway 24 in the block 22. The angular adjustment of the block 22 and hence the head support rod 60 and 62 is accomplished by withdrawing the pin 42 from the particular aperture, the withdrawn position being shown in phantom lines in FIG. 3, and inserting it in a desired angular position, according to the aperture which adjusts to that angle, as best shown in FIG. 7, such that the pins 42, in the slot or passageway 24 and the aperture 32 and the corresponding aperture in the block 28, fix the angular relationship of the head support rods with respect to the tongue or plate 10. The block 22 is securely hinged to the plate 10 by means of a hinge 50 which, in turn, is secured to the block by screws or fastening devices 52 and to the plate by rivets or other fastening devices 54. Obviously, the nature of these fastening devices is of little consequence so long as a sturdy, firm, securement is obtained.

The block 28, as best shown in FIG. 7, is secured by screws or other fastener 56. Again, the nature of the fastener is not critical. Similar fasteners secured the block 26 in position on the plate.

As previously described, the head support rods 60 and 62 extend in parallel fashion the apertures 22A and 22B in the block 22 and are maintained in their parallel relationship, although exact parallelism is not required, by the cross bar 64 which may be an integral bar or may be divided and attached by welding or other means.

As best shown in FIGS. 2 and 10, the halo support rod 66 is attached to the cross bar 64 by means of clamp 70 which clamp is shown in detail in FIG. 8. The clamp 70 comprises a number of components. The clamp 70, thus, includes a bolt 72 which, in the preferred embodiment, though not necessarily critical to the invention, includes a hexagonal head 74 and a knurled knumb screw head 76 which is welded or press-fitted to the proximal end of the bolt 72. The bolt 72 at its distal end is threaded at 76 and is received, as will be described, in a clamp block 80. The clamp block 80 is generally rectangular in configuration, although the outer configuration is of little consequence, includes a slot 82 and a circular passageway communicating with the slot, the passageway being shown at 84, to receive a rod such as the cross bar 64. The resulting configuration is, of course, a generally U-shaped block, one of the legs of the U having a threaded aperture 86 which receives the thread 76 on the screw 72. The other leg of the U includes a tapered aperture 88 which receives one of the tapered ends of a double tapered ferrule 100, as will be described.

The other clamping block 90 is also in a general U configuration, very similar to that just described with respect to block 80. The block 90 includes a slot 92, an aperture or passageway 94 to receive a rod 66. However, the passageway 96 receives the shaft of the bolt 72 and is not threaded. A tapered aperture 98, corresponding generally to that described with respect to tapered aperture 88, is provided to receive the other tapered end of the ferrule 100. A lock washer 78 is desirably, though not necessarily included. The lock washer is the split ring type conventionally used. Other types of lock washer may, of course, be used if a lock washer is desired.

It will be apparent from the examination of this structure how the clamping arrangement of clamp 70 operates. As the bolt 72 is threaded inwardly and tightened, it clamps the ferrule 100 in the tapered apertures 88 and 98 and clamps the two U-shaped clamp blocks 80 and 90 around the respective rods 64 and 66 and, in one operation, fixes the angular and positional relationships of the two rods 64 and 66. When it is desired to change this angular relationship, the clamp is simply loosened up and moved, turned, and twisted on the rods and is retightened at whatever position, angularly of the two rods respectively and longitudinally of each of the rods independently.

FIG. 9 shows in detail the clamping arrangement for securing the halo rings to the halo support rod. The general arrangement is, of course, shown in FIGS. 1 and 2. The halo ring 106 is provided with a plurality of threaded apertures. The apertures are, conventionally, threaded although unthreaded apertures and a nut or the keeper may be used with equal effect. In the exemplary embodiment, a screw 112 is threaded on the distal end, as shown at 114, to be threadably received in the threaded apertures of the halo ring 106. The screw is, in the preferred embodiment, provided at the proximal end with the hexagonal nut portion and a knurled ring portion, the knurled ring portion typically being welded are press-fitted around the nut portion, as shown in FIG. 9. Other end structures which permit tightening and loosening are, of course, satisfactory. A lock washer 120 is used to lock the screw in position when it is tight against the lock 122 which is secured by press-fitting, welding or some other means or integrally formed on the end of the halo support rod 66. An examination of FIG. 9 will render the operation of this clamping arrangement apparent. When it is desired to adjust the halo ring with respect to the end of the halo support rod, when the clamp 110 is simply loosened and the halo ring is adjusted and the clamp is tightened again, locking at rigid position with respect to the halo support rod 66.

Referring now to FIGS. 4 and 5, in particular, with general reference to the other figures, in use the halo jig of this invention is slipped under the mattress of the operating table or little, as shown in FIG. 4, upon which the patient will be placed or is already resting. The patient is then moved out, the surgeon holding the patient's head in proper position, to rest upon the head support rods 66 and 62. The angle of these rods is, of course, adjusted previously as may be desired, according to the apparatus and technique previously described herein. The halo ring is then placed around the patient's head, as shown in FIG. 5, and the halo support rod 66 is positioned and attached securely to the halo rings to hold the halo ring in exact positions. In the position as shown in FIG. 5, then the skull pins are easily and quickly inserted and torqued. The insertion of the torque pins in the halo ring is a conventional procedure and is used with all halo rings in generally the same manner. The aforecited references described this procedure in greater detail.

Once the halo ring is securely fastened to the patient by means of the conventional skull pins, then the function of the jig of this invention is generally completed. Its function being to keep the patient's head in the proper position while leaving the surgeon's hands free to manipulate the head, the patient, and to affix the skull pins. The halo support rod 66 is then loosened, by completely removing the screw 112 from the clamp 110 and the support rods are withdrawn, leaving the halo ring on the patient ready to be supported a halo vest, a Stryker frame or a standard bed. The attachment to the halo vest, or other supporting means, may also be made before removal of the halo support rod 66, if desired.

From the preceding description, it will be apparent that the invention described and claimed herein provides a very simple, safe and efficient apparatus to enable the surgeon to accurately and safely affix a halo ring to a patient, with minimal risk of entry to the patient and with maximum accuracy and safety.

Industrial Application

The jig of this invention may be used by orthopedic surgeons in attaching virtually any halo ring and may be used in hospitals and clinics throughout the world.

What is claimed is:

1. A jig for supporting a patient and the patient's head during the installation of a cervical halo comprising the combination of:

a plate adapted to be slipped under the mattress of a litter or operating table, the plate being so constructed and configured as to be held, in use, rigidly in place by the weight of the patient laying on the mattress;

a block assembly securely attached to the plate at the distal end thereof, the proximal end of the plate being adapted to extend under the patient, the block assembly comprising a block pivotally mounted near the distal end of the plate, means for adjusting the angle of the pivotally mounted block with respect to the plate, the pivotally mounted block having formed therein at least a pair of apertures to receive at least a pair of head support rods; and cervical halo support ring adjusting structure comprising at least a pair of head support rods adapted to be received in the apertures in the pivotally mounted block, a cross bar, a halo support rod, first means adjustably clamping the cross bar to the halo support rod, and second means for adjustably clamping a cervical halo to the halo support rod.

2. The apparatus of claim 1 wherein the clamping means for adjustably clamping the cross bar to the halo support rod comprises a pair of generally U-shaped clamping blocks, each of said U-shaped clamping blocks having a passageway through the legs of the U-shaped blocks forming in one leg of the U of each of the blocks a tapered aperture, a double-tapered ferrule adapted to be received in the respective tapered apertures of the aforesaid clamping blocks, and a bolt extending through the aperture in the clamping blocks being threadably received in at least one of the clamping blocks, the bolt, the ferrule, and the clamping blocks being so constructed and configured as to permit the tightening and loosening of the legs of the U configurations of the clamping blocks about the cross bar and the halo support rod respectively and the ferrule in the tapered apertures of the U legs of blocks by the tightening and loosening of the bolt.

3. The apparatus of claim 1 or claim 2 wherein the means for adjusting the angle of the pivotally mounted block comprises:

an additional block adjacent at least one end of the pivotally mounted block having formed therein a plurality of angularly related apertures;

the pivotally mounted block having formed therein a passage adapted to be aligned with the apertures, respectively at different angles, in the additional block; and a pin removably received through the aperture in the additional block and the passage in the pivotally mounted block to thereby fix the angular relationship of the pivotal block to the plate.

* * * * *